United States Patent [19]

Matsui et al.

[11] 4,010,182

[45] Mar. 1, 1977

[54] METHOD FOR PRODUCING N-(4-FLUOROPHENYL)-2,3,-DICHLOROMALEIMIDE

[75] Inventors: Kazuo Matsui, Fujisawa; Taichiro Shigematsu, Machida; Tetsuya Shibahara, Kawasaki; Makoto Nakazawa, Yokohama, all of Japan

[73] Assignee: Mitsubishi Chemical Industries Ltd., Tokyo, Japan

[22] Filed: May 7, 1975

[21] Appl. No.: 575,389

[30] Foreign Application Priority Data

May 15, 1974 Japan .................. 49-53978

[52] U.S. Cl. .................... 260/326.5 FM; 71/95
[51] Int. Cl.$^2$ .................... C07D 207/44
[58] Field of Search .................. 260/326.5 FM

[56] References Cited

UNITED STATES PATENTS

| | | | |
|---|---|---|---|
| 2,962,504 | 11/1960 | Walker et al. | 260/326.5 FM |
| 3,018,292 | 1/1962 | Sauers et al. | 260/326.5 FM |
| 3,129,225 | 4/1964 | Shapiro et al. | 260/326.5 FM |
| 3,148,195 | 9/1964 | Ladd | 260/326.5 FM |
| 3,734,927 | 5/1976 | Kawada et al. | 260/326.5 FM |
| 3,758,498 | 9/1973 | Pfuller et al. | 260/326.5 |

FOREIGN PATENTS OR APPLICATIONS

| | | | |
|---|---|---|---|
| 671,884 | 6/1972 | Japan | 260/326.5 FM |
| 712,681 | 10/1974 | Japan | 260/326.5 FM |
| 852,634 | 1/1957 | United Kingdom | 260/326.5 FM |

*Primary Examiner*—Richard J. Gallagher
*Assistant Examiner*—M. Vaughn
*Attorney, Agent, or Firm*—Lane, Aitken, Dunner & Ziems

[57] ABSTRACT

N-(4-fluorophenyl)-2,3-dichloromaleimide of uniform grain size is produced either by reacting 2,3-dichloromaleic acid, an anhydride or an ester thereof with 4-fluoroaniline in an aqueous medium or by dehydrative-cyclization of either N-(4-fluorophenyl)-2,3-dichloromaleamic acid or 4-fluoroanilinium 2,3-dichloromaleate in an aqueous medium. The N-(4-fluorophenyl)-2,3-dichloromaleimide of uniform grain size provides improved fungicidal activity and is convenient for preparing an agricultural fungicidal composition.

6 Claims, No Drawings

METHOD FOR PRODUCING N-(4-FLUOROPHENYL)-2,3,-DICHLOROMALEIMIDE

BACKGROUND OF THE INVENTION

1. Field of the Invention:

This invention relates to a method for producing N-(4-fluorophenyl)-2,3-dichloromaleimide which has excellent agricultural fungicidal activity.

2. Description of the Prior Art:

It has been reported that N-(4-fluorophenyl)-2,3-dichloromaleimide as expressed by the formula

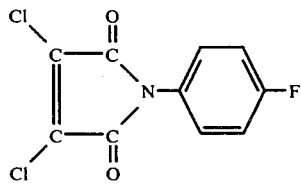

exhibits excellent activity as an agricultural fungicide and is effective for protecting plants from various diseases such as anthracnose rot of cucumbers (*Collectotrichum lagenarium*), late blight of tomatoes (*Phytophthora infestans*), citrus melanose (*diaporthe citri*), citrus scab (*elsinoe fawcetti*) and red dust disease of coffees (Japanese Pat. Nos. 712,681 and 671,884, U.S. Pat. No. 3,734,927, British Pat. No. 1,324,910, etc.)

From these patents, it is already known that N-(4-fluorophenyl)-2,3-dichloromaleimide can be produced either by reacting 2,3-dichloromaleic acid, an anhydride or an ester thereof with 4-fluoroaniline in an organic solvent or by the intra-molecular dehydration of N-(4-fluorophenyl)-2,3-dichloromaleamic acid in an organic solvent. Japanese Laid-open Patent Application Nos. Sho 49(1974)-110,661 and Sho 49(1974)-110,662 report that the reactions can be advantageously effected in the presence of a strong acid such as p-toluene-sulfonic acid which serves as a catalyst.

However, N-(4-fluorophenyl)-2,3-dichloromaleimide obtained by the above-mentioned conventional methods has a comparatively large grain size and therefore, must be pulverized two or more times for use as an agricultural fungicide. Moreover, the conventional reaction methods employ an organic solvent and accordingly require an additional operation for recovering the solvent and encounter the problem of corrosion of the apparatus by the reaction mixture. For example, when acetic acid is used as the organic solvent, an excessive amount of dichloromaleic acid, or one of the starting materials, dissolves in the acetic acid to form a solution which has extremely high corrosive action and attacks the centrifugal filter and the distillation apparatus employed for recovering the solvent. To eliminate this danger, expensive materials such as Monel metal or Hastelloy alloy C must be employed. When an aromatic hydrocarbon such as benzene is used as the organic solvent, the reaction cannot fully proceed unless a dehydrating agent or catalyst such as p-toluene-sulfonic acid is employed.

BRIEF SUMMARY OF THE INVENTION

It is therefore an object of this invention to provide a method for producing N-(4-fluorophenyl)-2,3-dichloromaleimide without the use of any organic solvent and catalyst.

Another object of this invention is to provide a method for producing, at a high yield, N-(4-fluorophenyl)-2,3-dichloromaleimide having excellent fungicidal activity and uniform grain size and therefore suitable for an agricultural fungicidal composition.

These and other objects of this invention will become apparent from reading the following description.

The characteristic feature of this invention resides in the use of an aqueous medium such as water as a reaction medium in the process of preparing N-(4-fluorophenyl)-2,3-dichloromaleimide, more specifically, the present invention is a method for preparing the imide by reacting a starting material selected from a group of dichloromaleic acid, anhydride and esters thereof with 4-fluoroaniline, or by dehydrative cyclization of either N-(4-fluorophenyl)-2,3-dichloromaleamic acid or 4-fluoroanilinium 2,3-dichloromaleate.

DETAILED DESCRIPTION OF THE INVENTION

In the formation of an imide in a dehydration reaction, it has been a common practice to use an organic solvent such as an aromatic hydrocarbon (benzene, toluene or xylene), a chlorinated alkane (chloroform or carbon tetrachloride), a ketone (acetone or methyl ethyl ketone), a lower alcohol (methanol or ethanol) or a lower fatty acid (acetic acid). In view of the chemical equilibrium it might seem that in a dehydrating reaction the presence of water in the reaction system as in the present invention would prevent the progress of the reaction and result in a remarkable reduction in the yield of the desired product. Actually, however, the inventors found that N-(4-fluorophenyl)-2,3-dichloromaleimide could be manufactured through a reaction in an aqueous medium at an increased yield as compared with a reaction in the presence of organic solvents. The inventors also found that other various advantages were obtained by a reaction in an aqueous medium.

The starting material as employed in this invention is selected from the group of 2,3-dichloromaleic acid, anhydride and esters thereof. These starting materials may be prepared in various ways. For example, dichloromaleic acid is prepared by oxydizing 3-formyl-2,3-dichloroacrylic acid with fuming nitric acid (Ber. 38 2588-90); dichloromaleic anhydride is prepared through reacting maleic anhydride with chlorine in the presence of iron (U.S.S.R. Pat. No. 43,419 and others); an ester of 2,3-dichloromaleic acid is readily prepared through reacting dichloromaleic acid or an anhydride thereof with a lower alcohol.

In the reaction of this invention 2,3-dichloromaleic acid, anhydride or an ester thereof may normally be used in the amount of 1–2 preferably in 1.0–1.3 mole per mole of 4-fluoroaniline. Although not critical, the quantity of water used as the reaction medium is preferably in the range of 2–20 times the amount of 4-fluoroaniline by weight.

When dichloromaleic acid or an anhydride thereof is used as the starting material, the reaction temperature is normally in the range of 10°–200° C, preferably 40°–150° C; when dichloromaleic acid ester is used, it is normally in the range of 0°–200° C, preferably 30°–120° C.

To react 2,3-dichloromaleic acid, an anhydride or an ester thereof with 4-fluoroaniline, the latter may be added to the former dropwise with mixing. In this case, however, if the reaction is carried out at higher temperature, for example at reflux temperatures, then by-products tend to be formed through the reaction of p-fluoroaniline with N-(4-fluorophenyl)-2,3-dichloromaleimide, thereby reducing the purity of the product. This danger may be eliminated by employment of a two-stage reaction method wherein the starting material is mixed with 4-fluoroaniline dropwise at comparatively lower temperatures (first stage) and then the reaction is completed at elevated temperatures (second stage) to minimize the formation of by-products. The reaction temperature for the first stage is lower than 60° C, preferably in the range of room temperature — 50° C; the reaction temperature for the second stage is preferably in the range of 60° C to reflux temperature. When the reaction is to be effected in a single stage, it is advisable to add 4-fluoroaniline dropwise into 2,3-dichloromaleic acid, an anhydride or an ester thereof. Whereas when a two-stage reaction is adopted, the desired product may be obtained at a similar high yield by adding the former to the latter dropwise or vice versa. The reaction time is not specially limited and may be selected within a wide range: the reaction may usually be fully completed within 1–6 hours. In the two-stage reaction the dropping time for the first stage may be in the range of 10–60 minutes and the reaction time for the second stage may be in the range of 1–6 hours. In this way the desired substance may be obtained at a high purity after completion of the reaction by merely cooling the reaction mixture and then separating the crystals by filtration.

As mentioned previously, the desired compound may alternatively be prepared by dehydrative-cyclization of either N-(4-fluorophenyl)-2,3-dichloromaleamic acid or 4-fluoroanilinium 2,3-dichloromaleate in an aqueous medium. The dehydrative-cyclization reaction may be effected by dissolving these substances in water and heating the solution at 50°–200° C, preferably 60°–150° C. The heating time may be selected within a wide range but normally 1–6 hours may be sufficient for the purpose. The quantity of water used as the reaction medium may normally be in the range of 2–20 times, preferably 3–15 times as much as the starting material used by weight. After completion of the reaction the product may be recovered in the same manner as previously described.

The starting material, 2,3-dichloromaleamic acid may be obtained by reacting, for example, 2,3-dichloromaleic anhydride and 4-fluoroaniline in an organic solvent at comparatively low temperatures. Another starting material, 4-fluoroanilinium 2,3-dichloromaleate may be obtained by reacting 4-fluoroaniline with 2,3-dichloromaleic acid at comparatively low temperatures (lower than 50° C). In this reaction, the reaction medium may be either water or any suitable solvent, but the use of water is preferred considering the solubility of dichloromaleic acid and the formed salt, and also considering that the reaction for producing the imide from the resulted salt is effected in an aqueous medium.

As previously described, according to this invention N-(4-fluorophenyl)-2,3-dichloromaleimide is prepared by reaction in an aqueous medium. This method is advantageous in that the reaction operation is more easily conducted as compared with conventional methods in which the reaction is carried out in an organic solvent and in that the previously mentioned various disadvantages encountered in the use of an organic solvent can be eliminated.

In this invention N-(4-fluorophenyl)-2,3-dichloromaleimide is obtained in the form of uniform particles having an average grain size of $10\mu$ and therefore, a single pulverizing treatment is sufficient for preparing an agricultural fungicidal composition from this product. Thus, the particle size obtained by the method of this invention simplifies the fungicidal composition preparation. This may be understood more fully from reading the following Example 1 which illustrates that N-(4-fluorophenyl)-2,3-dichloromaleimide prepared by a conventional method has an average grain size of as large as $700\mu$. Thus, a single pulverizing operation is not sufficient for reducing the grain size to provide the desired fungicidal activity and the pulverizing operation need be repeated more than twice. When applied as an agricultural fungicide, N-(4-fluorophenyl)-2,3-dichloromaleimide of a reduced average grain size seems to present an increased adhesive ratio onto the plant body and hence exhibits an enduring fungicidal effect.

In addition, as is apparent from the Examples below the reaction in an aqueous medium produces N-(4-fluorophenyl)-2,3-dichloromaleimide with a higher yield than the conventional methods.

The invention will be understood more fully from the following Examples. It is to be understood, however, that the invention is not limited only to these Examples but a number of changes and modifications will be apparent to those skilled in the art within the scope and spirit of this invention as defined in the appended claims.

EXAMPLE 1

10 g (0.06 mol) of 2,3-dichloromaleic acid was dissolved in 100 ml of water. Then, to the resulting solution 5.55g (0.05 mol) of 4-fluoroaniline was added dropwise over a period of 5 min. at reflux temperatures under agitation. Upon addition of 4-fluoroaniline, a white crystal separated out immediately but the reaction was allowed to preceed for two hours. After cooling, the crystal was separated by filtration and fully rinsed with water to obtain 12.7g (yield, 97.7%) of N-(4-fluorophenyl)-2,3-dichloromaleimide (Sample No. 1) having an average grain size of $10\mu$. An analysis by gas chromatography showed that the N-(4-fluorophenyl)-2,3-dichloromaleimide had a purity of 96.2%.

For the purpose of comparison, the 100 ml of water was replaced with 100 ml of glacial acetic acid and a similar operation was repeated. In this case 12.4g (yield, 93.0%) of N-(4-fluorophenyl)-2,3-dichloromaleimide (Sample No. 2) having an average grain size of $700\mu$ was obtained.

Sample Nos. 1 and 2 (each in an amount of 2kg) were subjected to pulverizing tests by use of a supersonic jet powdering machine Model No. PJM-100NP (manufactured by Japan Pneumatic Co. Ltd.). The air pressure was 5–7kg/cm$^2$ (air quantity, 2.1Nm$^3$/min) and the feed speed was 600g/min. The results were as listed in Table 1.

Table 1

| Sample No. | Average grain size of crystallized product | Average grain size of pulverized product | Number of times of pulverizing operation |
|---|---|---|---|
| 1 | $10\mu$ | $3.9\mu$ | 1 |

Table 1-continued

| Sample No. | Average grain size of crystallized product | Average grain size of pulverized product | Number of times of pulverizing operation |
|---|---|---|---|
| 2 | 700μ | 15.2μ | 1 |

Then wettable powders were prepared from the thus pulverized Sample Nos. 1 and 2. The composition was: N-(4-fluorophenyl)-2,3-dichloromaleimide, 78 weight parts; Kunirite 250 (carrier; available from Kunimine Koka Kagaku K.K.), 15 weight parts; Neopelex Powder No. 2 (surfactant; available from Kao Atras K.K.), 5 weight parts; Sanex P-501 (wetting and spreading agent; available from Sanyo Pulp Co., Ltd.), 2 weight parts. The resulted wettable powders were diluted with water to specified concentrations and the degree of protection against anthracnose rot in cucumbers (*Collectotrichum lagenarium*) was compared by pot tests. The results were as listed in Table 2.

Table 2

| Concentration (ppm) | [Protective value (%)] | |
|---|---|---|
| | Sample No. 1 | Sample No. 2 |
| 100 | 100 | 100 |
| 50 | 100 | 99.0 |
| 25 | 100 | 98.8 |
| 12.5 | 99.9 | 95.0 |
| 6.25 | 98.0 | 94.3 |
| 3.125 | 97.8 | 88.0 |
| 1.562 | 97.0 | 67.7 |

To inquire into the reason why the fungicidal effect varies as seen in the Table, the Samples were checked with respect to the distribution of their grain size after pulverization, their resistance to removal by rain by determination of deposited quantities on the plant body and their effect as fungicide.

The Sample Nos. 1 and 2 were again pulverized in the same manner as previously described except that this time the feed speed was set at 800g/min. After pulverization, the distribution of grain size was measured. The results were as set forth in Table 3.

Table 3

| Grain size (μ) | Distribution (wt%) | |
|---|---|---|
| | Sample No. 1 | Sample No. 2 |
| 2 – 3 | 27.1 | 0.8 |
| 3 – 4 | 23.5 | 1.8 |
| 4 – 5 | 24.4 | 3.5 |
| 5 – 6 | 11.3 | 3.0 |
| 6 – 7 | 6.8 | 4.4 |
| 7 – 8 | 3.1 | 6.3 |
| 8 – 9 | 3.0 | 11.6 |
| 9 – 10 | 0.8 | 6.4 |
| 10 – 19 | — | 51.2 |
| 19 – 29 | — | 11.0 |
| Average grain size (μ) | 4.2 | 12.6 |

Wettable powders were prepared from thus pulverized Sample Nos. 1 and 2. (The composition was identical to that previously described.) The powders were diluted with water to specified concentrations and applied to the potted saplings of Unshu tangerine placed on a turntable. After drying with air for several hours, water was sprinkled on the saplings for two hours at a rate of 100mm/hr by use of an artificial rainfall apparatus. After that, the quantity of imide remaining on the leaves was measured by gas chromatography. Table 4 represents the anti-rainfall properties of these samples in terms of their adhesiveness to the test plant body.

Table 4

| Dilution ratio (times) | Adhesive ratio (%) | |
|---|---|---|
| | Sample No. 1 | Sample No. 2 |
| 500 | 46.7 | 30.4 |
| 1000 | 42.7 | 33.6 |
| 2000 | 45.3 | 34.9 |

The adhesive ratio was calculated as follows:

$$\text{Adhesive ratio (\%)} = \frac{\text{Quantity adhering after sprinkling water}}{\text{Quantity adhering before sprinkling water}}$$

The fungicidal activities of the wettable powders was tested using tangerine saplings planted in a nursery having an area of approx. ½ are. For citrus melanose (diaporthe citri) a 800-time-diluted liquor was applied at intervals of 15 and 30 days; for citrus scab (elsinoe fawcetti) a 1000-time-diluted liquor was applied at an interval of 20 days. The infective ratio for each disease was as shown in Table 5.

Table 5

| | Diaporthe citri | | Elsinoe fawcetti |
|---|---|---|---|
| | 15-day interval | 30-day interval | |
| Sample No. 1 | 2.3 | 4.4 | 0.8 |
| Sample No. 2 | 12.0 | 18.9 | 7.5 |
| Untreated area | 58.3 | | 30.2 |

EXAMPLE 2

10g (0.06 mol) of 2,3-dichloromaleic anhydride was dissolved in 100 ml of water. Then, to the resulting solution 5.55g (0.05mol) of 4-fluoroaniline was added dropwise over a period of 5 min. at room temperatures under agitation. The mixture was allowed to react for 2 hours at 80° C. Upon cooling the reaction mixture, a crystal was separated out, which was then separated by filtration to obtain 12.8g of N-(4-fluorophenyl)-2,3-dichloromaleimide melting at 239°–242° C (not corrected) at a yield of 98.4%. An analysis by gas chromatography showed the product had a purity of 98.7%.

EXAMPLE 3

10g (0.06 mol) of 2,3-dichloromaleic anhydride was dissolved in 100 ml of water. Then to the resulting solution 5.55g (0.05 mol) of 4-fluoroaniline was added dropwise over a period of 5 min. at room temperatures under agitation. The mixture was then allowed to react for 15 hours at 60° C. Upon cooling the reaction mixture, precipitated crystal was separated by filtration to obtain 11.9g of N-(4-fluorophenyl)-2,3-dichloromaleimide melting at 239°–242° C (not corrected) at a yield of 91.5%. An analysis by gas chromatography showed the product had a purity of 97.9%.

EXAMPLE 4

10g (0.06 mol) of 2,3-dichloromaleic anhydride was dissolved in 200 ml of water. Then to the resulting solution 5.55g (0.05 mol) of 4-fluoroaniline was added dropwise over a period of 5 min. at room temperature under agitation. The mixture was then allowed to react for 2 hours at reflux temperatures. Upon cooling the reaction mixture, precipitated crystal was separated by filtration to obtain 12.9g of N-(4-fluorophenyl)-2,3-dichloromaleimide melting at 240°–243° C (not corrected) at a yield of 99.2%. An anaylsis by gas chromatography showed the product had a purity of 99.3%.

EXAMPLE 5

5.55g (0.05 mol) of 4-fluoroaniline was emulsified in 150 ml of water. Then to the resulting emulsion 10g (0.06 mol) of 2,3-dichloromaleic anhydride in 50 ml of water was added dropwise over a period of 30 min. at room temperatures under agitation. The mixture was then allowed to react at reflux temperatures. Upon cooling the reaction mixture, a crystal was removed out, which was separated by filtration to obtain 12.9g of N-(4-fluorophenyl)-2,3-dichloromaleimide melting at 240°–243° C (not corrected) at a yield of 99.1%. An analysis by gas chromatography showed the product had a purity of 98.6%.

EXAMPLE 6

Example of preparing N-(4-fluorophenyl)-2,3-dichloromaleamic acid 8.35g (0.05 mol) of 2,3-dichloromaleic anhydride was dissolved in 50 ml of benzene. To the resulting solution 20 ml of benzene solution containing 5.55g (0.05 mol) of 4-fluoroaniline was added dropwise over a period of 20 min. at temperatures of 5°–10° C under agitation. After completing the addtion, the mixture was agitated at 5°–10° C for 30 min. to form crystals, which were separated by filtration and washed with benzene to obtain 13.15g of N-(4-fluorophenyl)-2,3-dichloromaleamic acid in the form of white crystal melting at 222°–225° C (yield, 95%). The results of elementary analysis were as follows:

| $C_{10}H_3O_3NCl_2F$ | C | H | N | Cl |
|---|---|---|---|---|
| Calculated value (%) | 43.19 | 2.18 | 5.04 | 25.50 |
| Analytical value (%) | 42.86 | 2.01 | 4.72 | 25.10 |

11.2g of N-(4-fluorophenyl)-2,3-dichloromaleamic acid was suspended in 80 ml of water and allowed to react for two hours at reflux temperatures. Upon cooling the reaction mixture, precipitated crystals were separated by filtration to obtain 9.8g of N-(4-fluorophenyl)-2,3-dichloromaleimide melting at 239°–242° C (not corrected) at a yield of 94.0%. An analysis by gas chromatography showed the product had a purity of 99.5%.

EXAMPLE 7

9.25g (0.05 mol) of 2,3-dichloromaleic acid was dissolved in 50 ml of benzene. To the resulting solution 20 ml of benzene containing 5.55g (0.05 mol) of 4-fluoroaniline was added dropwise over a period of 20 min. at temperatures of 15°–25° C under agitation. After completing the addition, the mixture was agitated at that temperature for 30 min. during which time crystals formed, which were separated by filtration and washed with benzene to obtain 14.7g of 4-fluoroanilinium 2,3-dichloromaleate in the form of white crystal at a yield of 98.7%. The crystal had a melting point (decomposition point) of 207° C and is expressed by the following formula:

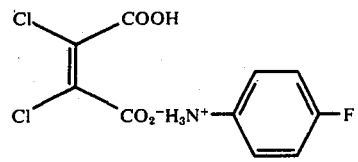

The results of elementary analysis were as follows:

| $C_{10}H_4NO_4Cl_2F_1$ | C | H | N | Cl | F |
|---|---|---|---|---|---|
| Calculated value (%) | 40.56 | 2.72 | 4.73 | 23.95 | 6.42 |
| Analytical value (%) | 40.69 | 2.73 | 4.79 | 24.08 | 6.89 |

5.56g of the thusly resulted 4-fluoroanilinium 2,3-dichloromaleate was suspended in 40 ml of water and allowed to react for 2 hours at reflux temperatures. Upon cooling the reaction mixture, precipitated crystal was separated by filtration to obtain 4.8g of N-(4-fluorophenyl)-2,3-dichloromaleimide melting at 240°–242° C (not corrected) at a yield of 95.0%. An analysis by gas chromatography showed the product had a purity of 99.2%.

EXAMPLE 8

18.5g (0.1 mol) of 2,3-dichloromaleic acid was dissolved in 120 ml of water. To the resulting solution 8.9g (0.08mol) of 4-fluoroaniline was added dropwise over a period of 5 min. at reflux temperatures under agitation. The mixture was then allowed to react for 2 hours at reflux temperatures. Upon cooling the reaction mixture, precipitated crystal was separated by filtration to obtain 20.3g of N-(4-fluorophenyl)-2,3-dichloromaleimide melting at 239°–240° C (not corrected) at a yield of 98.1%. An analysis by gas chromatography showed the product had a purity of 95.5%.

EXAMPLE 9

15g (0.07 mol) of dimethyl 2,3-dichloromaleate was added to 100 ml of water. To the resulting solution 6.7g (0.06 mol) of 4-fluoroaniline was added dropwise over a period of 5 min. at reflux temperatures under agitation. The mixture was then allowed to react for 2 hours at reflux temperatures. Upon cooling the reaction mixture, precipitated crystal was separated by filtration to obtain 15.2g of N-(4-fluorophenyl)-2,3-dichloromaleimide melting at 240°–242° C (not corrected) at a yield of 97.3%. An analysis by gas chromatography showed the product had a purity of 94.1%.

EXAMPLE 10

8.35g (0.05 mol) of 2,3-dichloromaleic anhydride was dissolved in 20 ml of water. To the resulting solution an emulsion prepared from 5.55g (0.05 mol) of 4-fluoroaniline and 10 ml of water was added dropwise over a period of 30 min. After completing the additon, the reaction mixture was stand for 10 min. and precipitated crystal was separated by filtration to obtain 13.6g of 4-fluoroanilinium 2,3-dichloromaleate at a yield of 92%. The salt was identical with that produced in Example 7 and had a melting point (decomposition point) of 207° C.

What is claimed is:

1. In a process for the preparation of N-(4-fluorophenyl)-2,3-dichloromaleimide by reaction of a first reactant selected from the group consisting of 2,3-dichloromaleic acid, 2,3-dichloromaleic anhydride and esters of 2,3-dichloromaleic acid with 4-fluoroaniline as a second reactant or by dehydrative-cyclization reaction of N-(4-fluorophenyl)-2,3-dichloromaleamic acid or 4-fluoroanilinium-2,3-dichloromaleate, the improvement characterized by conducting the reaction in water.

2. The process of claim 1 wherein the amount of said water is 2 to 20 times by weight based on the weight of 4-fluoroaniline and the N-(4-fluorophenyl)-2,3-dichloromaleimide is prepared from said first and second reactants.

3. The process of claim 1 wherein the amount of said water is 2 to 20 times the weight of the reactants and the N-(4-fluorophenyl)-2,3-dichloromaleimide is prepared by dehydrative-cyclization of N-(4-fluorophenyl)-2,3-dichloromaleamic acid or 4-fluoroanilinium 2,3-dichloromaleate.

4. The process of claim 2 wherein said reaction is carried out by reacting said first reactant with 4-fluoroaniline in a mole ratio of 1.3:1.

5. The process of claim 1 wherein said reaction is conducted in two stages at different temperatures and wherein the N-(4-fluorophenyl)-2,3-dichloromaleimide is prepared by reacting said first reactant with 4-fluoroaniline.

6. The process of claim 5 wherein the first stage of said reaction is carried out at a temperature in the range of from room temperature to 60° C and the second stage of said reaction is subsequently carried out at a temperature in the range of 60° C to reflux temperature.

* * * * *